(12) United States Patent
Lucero et al.

(10) Patent No.: US 12,665,093 B2
(45) Date of Patent: Jun. 23, 2026

(54) SYSTEMS FOR MACHINE-LEARNED RESOURCE AVAILABILITY DETERMINATION FOR A POPULATION

(71) Applicant: Express Scripts Strategic Development, Inc., St. Louis, MO (US)

(72) Inventors: David Lucero, Queens, NY (US); Andrew Vinson, Jackson Heights, NY (US); Samuel Affare, O'Fallon, MO (US); Alexi E. Makarkin, Rolla, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 47 days.

(21) Appl. No.: 18/641,645

(22) Filed: Apr. 22, 2024

(65) Prior Publication Data

US 2025/0329471 A1     Oct. 23, 2025

(51) Int. Cl.
      *G16H 70/00*        (2018.01)
      *G16H 50/70*        (2018.01)
(52) U.S. Cl.
      CPC ............. *G16H 70/00* (2018.01); *G16H 50/70* (2018.01)
(58) Field of Classification Search
      CPC ............................... G16H 70/00; G16H 50/70
      USPC ........................................ 705/2–3
      See application file for complete search history.

(56) References Cited

U.S. PATENT DOCUMENTS

| | | | |
|---|---|---|---|
| 8,386,295 B2 | 2/2013 | Cheng | |
| 9,959,864 B1 | 5/2018 | Ingmarsson | |
| 9,977,959 B2 | 5/2018 | Dhein | |
| 10,431,214 B2 | 10/2019 | Guo | |
| 10,452,733 B2 | 10/2019 | Behm | |
| 10,664,570 B1 * | 5/2020 | Clark | ..................... G06F 3/0482 |
| 10,777,188 B2 | 9/2020 | Van Hout | |
| 2007/0043770 A1 | 2/2007 | Goodrich | |

(Continued)

FOREIGN PATENT DOCUMENTS

WO        2020049404 A2      3/2020

OTHER PUBLICATIONS

Letellier et al., How do environmental characteristics jointly contribute to cardiometabolic health? A quantile g-computation mixture analysis. Prev Med Rep. Sep. 26, 2022 30:102005. doi: 10.1016/j.pmedr.2022.102005. PMID: 36245803; PMCID: PMC9562428 (Year: 2022).*

(Continued)

*Primary Examiner* — Joy Chng
(74) *Attorney, Agent, or Firm* — Miller Johnson

(57)                ABSTRACT

A method for determining a social health score for a region includes receiving first data for a geographical area. The first data includes values for multiple features corresponding to multiple domains (such as economic, education, and environmental). The method includes, for a first domain, selecting a first set of features (for example, an environmental domain may include a feature that describes the amount of the geographical area covered by impervious surfaces), and determining weights for the first set of features. The method includes receiving second data for the region and determining a first region domain score based on the second data and the first feature weights. The method includes determining a total score for the region based on the first region domain score that indicates a level of resource access for a population of the region.

20 Claims, 7 Drawing Sheets

(simplified)

(56)      References Cited

U.S. PATENT DOCUMENTS

| | | |
|---|---|---|
| 2013/0179230 A1 | 7/2013 | Antoun |
| 2013/0309638 A1 | 11/2013 | Self |
| 2017/0039450 A1 | 2/2017 | Zhou |
| 2021/0174968 A1* | 6/2021 | Butterfield .......... G06F 18/2135 |
| 2021/0319887 A1* | 10/2021 | Derrick, Jr. .......... A61B 5/7275 |
| 2022/0139518 A1 | 5/2022 | Shawver |

OTHER PUBLICATIONS

Bodenreider et al., Healthy Places Index (3.0), Public Health Alliance of Southern California, https://www.healthyplacesindex. org/, Sep. 20, 2022 (Year: 2022).*
Bodenreider, et al., Healthy Places Index (3.0), Public Health Alliance of Southern California, https://www.healthyplacesindex. org/, Sep. 20, 2022.
CDC, Health Outcomes Measure Definitions, https://www.cdc.gov/ places/measure-definitions/health-outcomes/index.html, accessed at least as early as Jan. 8, 2024.
Keil, Alexander P., et al. "A quantile-based g-computation approach to addressing the effects of exposure mixtures." Environmental health perspectives 128.4 (Apr. 2020): 047004.
Keil, Package 'qgcomp', Aug. 10, 2023, https://cran.r-project.org/ web/packages/qgcomp/qgcomp.pdf.
Keil, qgcomp, https://github.com/alexpkeil1/qgcomp/blob/main/inst/ fig/res1.png, accessed at least as early as Jan. 8, 2024.
Letellier N, Zamora S, Yang JA, Sears DD, Jankowska MM, Benmarhnia T. How do environmental characteristics jointly contribute to cardiometabolic health? A quantile g-computation mixture analysis. Prev Med Rep. Sep. 26, 2022;30:102005. doi: 10.1016/j. pmedr.2022.102005. PMID: 36245803; PMCID: PMC9562428.
USALEEP, US Small-Area Life Expectancy Estimates Project—USALEEP, https://www.cdc.gov/nchs/nvss/usaleep/usaleep.html, accessed at least as early as Jan. 8, 2024.
World Health Organization, Social Determinants of Health, https:// www.who.int/health-topics/social-determinants-of-health#tab=tab_ 1, accessed at least as early as Jan. 8, 2024.

* cited by examiner

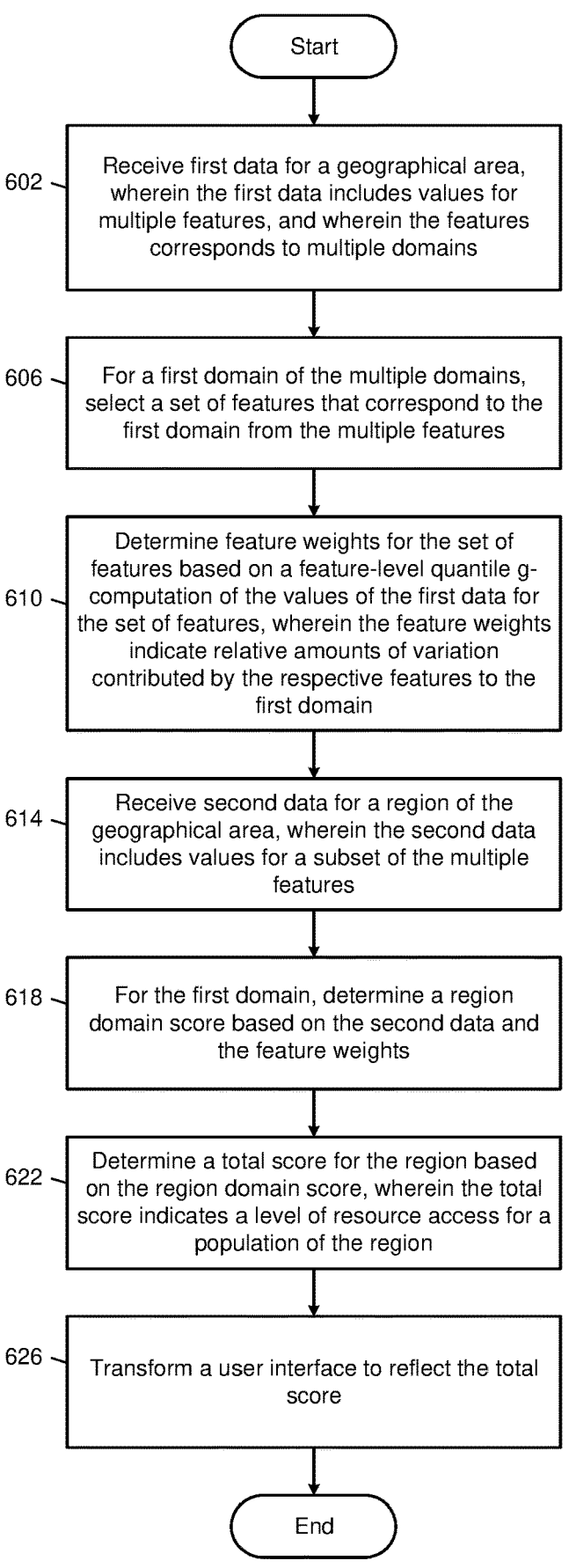

Start

602 — Receive first data for a geographical area, wherein the first data includes values for multiple features, and wherein the features corresponds to multiple domains 606 — For a first domain of the multiple domains, select a set of features that correspond to the first domain from the multiple features 610 — Determine feature weights for the set of features based on a feature-level quantile g-computation of the values of the first data for the set of features, wherein the feature weights indicate relative amounts of variation contributed by the respective features to the first domain 614 — Receive second data for a region of the geographical area, wherein the second data includes values for a subset of the multiple features 618 — For the first domain, determine a region domain score based on the second data and the feature weights 622 — Determine a total score for the region based on the region domain score, wherein the total score indicates a level of resource access for a population of the region 626 — Transform a user interface to reflect the total score End FIG. 6
(simplified)

SYSTEMS FOR MACHINE-LEARNED RESOURCE AVAILABILITY DETERMINATION FOR A POPULATION

FIELD

The present disclosure relates to computerized data processing of geographically-dependent data.

BACKGROUND

Social factors play a significant role in people's lives, including their overall health and access to health-related resources. Available resources, or lack thereof, in the vicinity of a person's neighborhood are often indicators of the health outcomes for the person, their family, and their community. There is a direct correlation between social conditions such as social determinants of health (SDoH) and health outcomes for a population. Some social factors that commonly affect the health outcomes of a population include access to education, access to food, medical infrastructure, financial conditions, and environmental conditions. These factors combined can at least partially determine a community's life expectancy. Quantifying these factors can educate organizations on needs of these communities to effectively provide access to resources that can lead to an improvement in health of the community.

One way to quantify the social factors affecting the social health of communities is to score each community based on the existing social conditions prevalent in the community. Existing scoring methodologies do not account for at least one of: (i) all social factors affecting health outcomes, (ii) domain level effects of social factors, or (iii) varying levels of effects of different social factors on the health outcome of a community. However, learning how changes in each social factor can affect the health outcome of a community differently than other social factors can assist in tailoring distribution of resources to communities for a larger overall impact.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer-implemented method for determining a social health score for a region includes receiving first data for a geographical area. The first data includes values for a plurality of features. The plurality of features corresponds to a plurality of domains. The method includes, for a first domain of the plurality of domains from the plurality of features, selecting a first set of features that correspond to the first domain, and determining first feature weights for the first set of features based on a feature-level quantile g-computation of the values of the first data for the first set of features. The first feature weights indicate relative amounts of variation contributed by the respective features to the first domain. The method includes receiving second data for the region of the geographical area. The second data includes values for a subset of the plurality of features. The method also includes, for the first domain, determining a first region domain score based on the second data and the first feature weights. The method includes determining a total score for the region based on the first region domain score. The total score indicates a level of resource access for a population of the region. The method includes transforming a user interface to reflect the total score.

In other features, the total score indicates a level of impediment for the population of the region of the geographical area to access resources. In other features, the method includes determining feature scores for the subset of the plurality of features by cross-multiplying the first feature weights and the values of the second data, and determining the first region domain score based on the feature scores. In other features, determining the first region domain score includes aggregating the feature scores.

In other features, the method includes for a second domain of the plurality of domains from the plurality of features, selecting a second set of features that correspond to the second domain, and determining second feature weights for the second set of features based on the feature-level quantile g-computation of the values of the first data for the second set of features. The second feature weights indicate relative amounts of variation contributed by the respective features to the second domain. The method includes, for the second domain, determining a second region domain score based on the second data and the second feature weights, the total score of the region is based on aggregating the first region domain score and the second region domain score.

In other features, there is a one-to-one correspondence between the first feature weights and the first set of features. In other features, the computer-implemented method includes in response to the subset being a proper subset, fill in those missing features of the second data. In other features, the region is a United States census tract.

In other features, the method includes determining a domain score for the first domain based on the first feature weights and the first data. The method includes determining a domain weight for the first domain based on a domain-level quantile g-computation applied to the domain score. The domain weight indicates a relative variation the first domain contributes to the geographical area. determining the first region domain score based on the domain weight.

In other features, the method includes determining feature scores based on cross-multiplying the first feature weights and the values of the second data, and determining the first region domain score based on cross-multiplying the domain weight and the feature scores. In other features, the plurality of domains includes seven domains, and the plurality of features includes twenty-eight features. In other features, the method includes preprocessing the values for the plurality of features to fit within a range. In other features, fitting the values within the range includes changing at least one value that is lower than the range to a minimum value of the range. In other features, fitting the values within the range includes changing at least one value that is higher than the range to a maximum value of the range. In other features, none of the first feature weights are below five percent.

In other features, the first data includes a plurality of life expectancy values for a plurality of regions of the geographical area, a plurality of rural status values for the plurality of regions, and a plurality of census region values for the plurality of regions. The first feature weights are determined based on the plurality of life expectancy values, the plurality of rural status values, and the plurality of census region values.

A system for determining a scoring a region includes a database including first data for a geographical area. The first data includes values for a plurality of features. The plurality of features corresponds to a plurality of domains, and second data for the region of the geographical area. The second data includes values for a subset of the plurality of features. The system includes a weighting module configured to, for a first domain of the plurality of domains from the plurality of features, select a first set of features that correspond to the first domain, and determine first feature weights for the first set of features based on a feature-level quantile g-computation of the values of the first data for the first set of features. The first feature weights indicate relative amounts of variation contributed by the respective features to the first domain. The system includes a domain scoring module configured to determine, for the first domain, a first region domain score based on the second data and the first feature weights. The system also includes a region scoring module configured to determine a total score for the region based on the first region domain score. The total score indicates a level of resource access for a population of the region. a user interface to reflect the total score.

In other features, the domain scoring module is configured to determine feature scores for the subset of the plurality of features by cross-multiplying the first feature weights and the values of the second data, and determining the first region domain score based on the feature scores. In other features, the weighting module is configured to, for a second domain of the plurality of domains from the plurality of features, select a second set of features that correspond to the second domain, and determine second feature weights for the second set of features based on the feature-level quantile g-computation of the values of the first data for the second set of features. The second feature weights indicate relative amounts of variation contributed by the respective features to the second domain. The domain scoring module is configured to, for the second domain, determine a second region domain score based on the second data and the second feature weights. The region scoring module is configured to determine the total score of the region based on aggregating the first region domain score and the second region domain score.

A non-transitory computer-readable medium includes instructions including receiving first data for a geographical area. The first data includes values for a plurality of features. The plurality of features corresponds to a plurality of domains. The instruction including, for a first domain of the plurality of domains from the plurality of features, selecting a first set of features that correspond to the first domain, and determining first feature weights for the first set of features based on a feature-level quantile g-computation of the values of the first data for the first set of features. The first feature weights indicate relative amounts of variation contributed by the respective features to the first domain. The instruction including receiving second data for a region of the geographical area. The second data includes values for a subset of the plurality of features. The instructions also including, for the first domain, determining a first region domain score based on the second data and the first feature weights. determining a total score for the region based on the first region domain score. The total score indicates a level of resource access for a population of the region. Further, the instructions including transforming a user interface to reflect the total score.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 6 is a flowchart of a second computer-implemented method for determining social health of a region according to aspects of the present disclosure.

In the drawings, reference numbers may be reused to identify similar and/or identical elements.

DETAILED DESCRIPTION

Introduction

Figure 1:
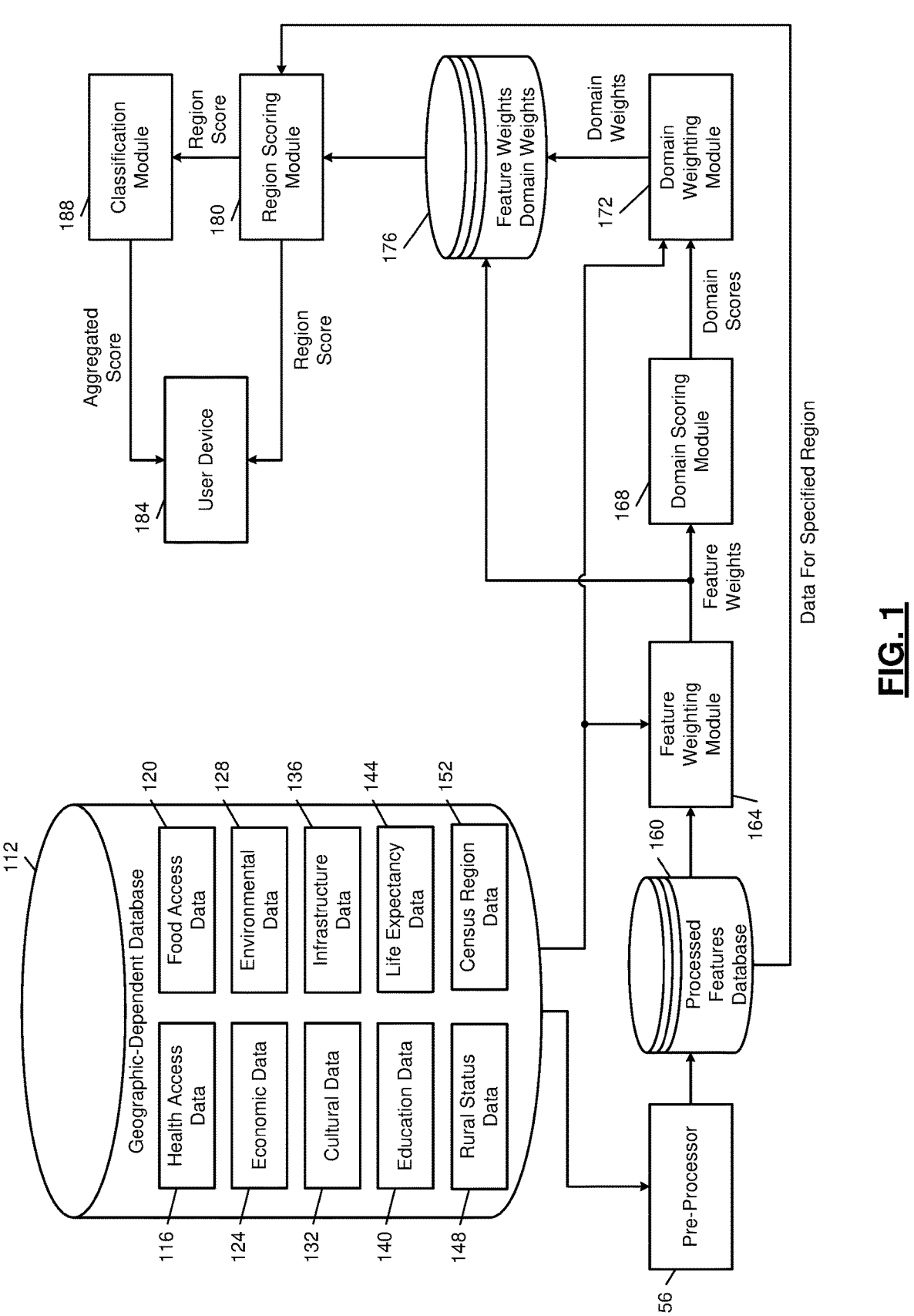
FIG. 1 is a block diagram illustrating an overview of an architecture for determining social health according to aspects of the present disclosure.

FIG. 1 shows an overview of an architecture for processing data records relative to a geography, e.g., determining social health for a region according to aspects of the present disclosure. The social health of a region can be determined as a region score based on social and environmental factors affecting a population of that region. The score can be derived by computing the effect of social resources available to the population on the health outcomes for the population. The social factors can be categorized within broader domains, such as economic, education, culture, infrastructure, food access, health access, and environment. Each domain can include values for multiple features that cumulatively define the social factors that impact the health of a population. In some examples, the social factors may be divided into multiple domains, e.g., seven domains, and multiple features, e.g., twenty-eight features.

For example, an education domain may include features such as a percentage of the regional population aged twenty-five (25) and over without a high school diploma, a percentage of the population aged 25 and over with a bachelor's degree or higher education, a health literacy ratio relative to a national average, and a percentage of the population between three (3) years and four (4) years of age enrolled in public or private educational institutions. An economic domain may include features such as a percentage of owner-occupied housing units, a median household income as a ratio with respect to a baseline (such as a local/regional median household income), a percentage of renter households spending more than fifty (50) percent of their income on rent, a percentage of the civilian labor force without an income source, and a percentage of households below the federal poverty line.

A weight defining the effect of a feature on the domain can be determined based on known values of features of the domain for each region and the life expectancy of the regions. A weight defining the effect of a domain on overall social health of the regions of the geographical area can be determined based on aggregated values of features of the domain for each region and the life expectancy of the regions. The weights can then be used to determine the scores for each of the regions.

A geographic-dependent database 112 may store values for features of regions of a geographical area. For example, the geographic-dependent database 112 may include data related to various census tracts within the United States. For example, the US Census Bureau defines census tracts as small, relatively permanent geographic entities within counties (or similar) of the United States, each including between 2,500 and 8,000 residents. The geographic areas may be designed, when first established, to be as homogeneous as possible with respect to population characteristics, economic status, and living conditions, as is the case with census tracts. In various implementations, geographic areas may be adjusted over time to maintain homogeneity.

The geographic-dependent database 112 may include values for features of domains for the regions. Various organizations, including but not limited to national government organizations and private research organizations, publish statistical information regarding regions within a geographical area. For example, the US Census Bureau published, at various times in the years 2015-2023, US Census Bureau American Community Survey including census tract data including geographical tracts across the United States and data pertaining to the tracts such as housing, infrastructure, education, economic, and health data for the tracts. The Centers for Disease Control (CDC) published life expectancy data and health data for the census tracts, and Environmental Protection Agency (EPA) published environmental data for the United States within the same time period. As another example, Food Access Research Atlas is a publicly available database that includes food access data for populations of the corresponding census tracts. Similarly, the National Walkability Index, National Assessment of Adult Literacy dataset, the United States Small-Area Expectancy Project measures, American Community Survey data, and the EPA's Toxic Release Inventory are examples of publicly available databases that provide tract-level information for the United States. The values for various features for each region (such as a tract) can be derived or extracted from such publicly available databases.

The geographic-dependent database 112 may store/include, for each region of a geographical area, values for features of each of the domains. In that regard, the geographic-dependent database 112 may include some or all of health access data 116, food access data 120, economic data 124, environmental data 128, cultural data 132, infrastructure data 136, and education data 140. In some examples, some of the features for one or more regions may not have a corresponding value, such as when a value is missing in the publicly available data. The data types may be stored in records within the geographic-dependent database 112. The features detailed below are for example purposes only, and different and additional features can be defined and stored. The health access data 116 may include values for features of the health access domain, such as those related to the health resources available to a population of the region. For example, for each region, the health access data 116 may include values corresponding to a percentage of the population of the region living with a disability, a percentage of the population of the region without health insurance, a population-to-primary care physician ratio for the region, and population-to-pharmacy ratio.

In some examples the population-to-primary care physician ratio may be based on dividing the region's population by a number of primary care physicians working within the region plus a 1-mile buffer around the region. Similarly, in some examples, the population-to pharmacy ratio may be based on dividing the region's population by a number of pharmacies located within the region plus a buffer distance, e.g., a 1-mile buffer around the region. The distances described herein can be adjusted to a buffer distance appropriate for the data in view of the population in that area.

The food access data 120 may include, for each region, values for features for the food access domain, such as those related to nutritional resources available to the population of the region. For example, the food access data 120 may include, for each region, values corresponding to a percentage of low income individuals that are beyond (i) one mile for an urban region or (ii) ten miles for a rural region from a supermarket, a percentage of households without vehicle that are beyond (i) one mile for an urban region or (ii) ten miles for a rural region from a supermarket, a percentage of households receiving public nutrition support (such as Supplemental Nutrition Assistance Program (SNAP) benefits), and a walkability score.

The cultural data 132 may include, for each region, values for features for the cultural domain, such as those related to cultural factors related to use or availability of healthcare resources. For example, the cultural data 132 may include, for each region, values corresponding to a percentage of households made up of one person living alone, a percentage of the population aged five and older that speaks a national language (such as English for United States regions), and a percentage of households that submitted responses to a census survey (such as the 2020 United States Census).

The infrastructure data 136 may include, for each region, values for features for the infrastructure domain, such as those related to housing resources available to the population of the region. For example, the infrastructure data 136 may include, for each region, values corresponding to a median house value as a ratio with respect to a baseline, a percentage of households without broadband (such as cable television, fiber optic, or Digital Subscriber Line), and a percentage of housing units that are unoccupied, a percentage of labor force that works from home or uses public transportation, walks or uses a bicycle to get to and from work.

The economic data 124 may include, for each region, values for features of the economic domain, such as those related to financial resources available to the population of the region. For example, the economic data 124 may include, for each region, values for features such as a percentage of owner-occupied housing units, a median household income as a ratio with respect to a baseline, a percentage of renter households spending more than fifty (50) percent of their income on rent, a percentage of the civilian labor force without an income source, and a percentage of households below the federal poverty rate.

The environmental data 128 may include, for each region, values for features of the environmental domain, such as those related to environmental characteristics of the region. For example, the environmental data 128 may include, for each region, values for features such as a mean value for particle matters less than 2.5 micrometers in diameter that pose health risks ("Particle Matter 2.5"), a percentage of area of the region plus one mile radius occupied by impervious surfaces, a percentage of the region within one mile of a hazardous waste site, and a pollution concentration per capita.

In some examples, mean values for Particle Matter 2.5 may be calculated using the pixel value average within the region boundaries, and missing values may be imputed/ filled-in with known values for neighboring regions. In some examples, an access to green space within the region plus a one mile buffer around the region and thirty by thirty meter land use rasters may be used to estimate an area of a region occupied by impervious surfaces. The area covered by impervious surfaces can be divided by the total area of the region to determine the percentage of the region occupied by impervious surfaces. In some examples, a percentage of a region within one mile of a hazardous waste site may be determined by dividing areas including a one mile buffer around each site in the Environmental Protection Agency's publicly-available Toxic Release Inventory by the total area of the region.

The education data 140 may include, for each region, values for features of the education domain, such as those related to educational acumen of and availability of educational resources to the population of the region. For example, the education data 140 may include, for each region, values for features such as a percentage of the regional population aged twenty-five (25) and over without a high school diploma, a percentage of the population aged 25 and over with a bachelor's degree or higher education, a health literacy ratio relative to the national average, and a percentage of the population between three (3) years and four (4) years of age enrolled in public or private educational institutions.

The geographic-dependent database 112 may further include life expectancy data 144, rural status data 148, and census region data 152 for each of the regions of the geographical area. The life expectancy data 144 includes, for each region, a life expectancy value or a known health outcome value (for example, a value between 50 and 100) for the population of the region indicating an expected overall health outcome for the population. The rural status data 148 includes for each region, a value of zero or one. A value of zero indicates that the region includes a rural area, and a value of one indicates that the region includes an urban area. The value indicates whether the population-weighted centroid of a region is in an urban or rural area. In some examples, such as in the Bureau of the Census urbanized area definitions, urban and rural areas may be defined such that a rural area is sparsely populated region with a population of fewer than 2,500 people, and an urban area is a region with a population of more than 2,500 people. A region may be associated with a rural status value of one if the geographic centroid of the region is in an area with a population of more than 2,500 people; and all other regions may be associated with a value of zero.

The census region data 152 may include a value, for each region, indicating where the region is located within the geographical area. For example, the census region data 152 for the geographical area covering the United States may indicate that a region is located in the Northeast, Midwest, South, or West area of the United States. A region located within the state of Connecticut, Massachusetts, New Hampshire, Rhode Island, Vermont, New Jersey, New York, or Pennsylvania may be associated with a Northeast indicator in the census region data 152; whereas, a region located within the state of Illinois, Indiana, Michigan, Ohio, Wisconsin, Iowa, Kansas, Minnesota, Missouri, Nebraska, North Dakota or South Dakota may be associated with a Midwest indicator in the census region data 152. Similarly, a region located within the state of Delaware, District of Columbia, Florida, Georgia, Maryland, North Carolina, South Carolina, Virginia, West Virginia, Alabama, Kentucky, Mississippi, Tennessee, Arkansas, Louisiana, Oklahoma, or Texas may be associated with a South indicator in the census region data 152; whereas, a region located within the state of Arizona, Colorado, Idaho, Montana, Nevada, New Mexico, Utah, Wyoming, Alaska, California, Oregon or Washington may be associated with a West indicator in the census region data 152. In some examples, the census region data 152 may divide the geographical area into sections based on the cost of living in the sections in comparison to the rest of the geographical area.

As input, the pre-processor 156 may receive region data for all regions of the geographical area from the geographic-dependent database 112. The region data may include health access data 116, food access data 120, economic data 124, environmental data 128, cultural data 132, infrastructure data 136, and education data 140 for all regions of the geographical area for preprocessing. The pre-processor 156 may be configured to standardize and normalize the region data such that all data is in a set of preferred formats and/or scales.

The pre-processed region data may be stored in the processed features database 160. In some examples, the processed features database 160 may be located within the geographic-dependent database 112. In some examples, the processed features database 160 may be separate and/or located distinctly from the geographic-dependent database 112. In some other examples, the processed features database 160 may be the same as geographic-dependent database 112 with the input region data replaced by the pre-processed region data.

A feature weighting module 164 may be configured to, for each domain, determine feature weights for the features of the domain based on the pre-processed region data. The feature weighting module 164 may take as input the pre-processed region data corresponding to a domain and apply the values for the features of that domain to a quantile g-computation model to determine weights for each feature. The feature weights may indicate relative amounts of variation contributed by the respective features to the domain. A quantile g-computation model may be used to estimate the parameters of a marginal structural model that characterizes the change in the expected potential outcome given a joint intervention on all exposures, possibly conditional on confounders. The quantile g-computation model may use a general health outcome (such as the life expectancy data 144) as a dependent variable, feature values as independent variables, and the rural status data 148 and the census region data 152 as covariates. The feature weighting module 164 may output a weight for each feature of the domain. The feature weighting module 164 can perform the same process on all domains to determine feature weights for every domain. The feature weighting module 164 may provide the feature weights to the domain scoring module 168 to generate domain scores and to the database 176 for storing.

The domain scoring module 168 is configured to receive the feature weights from the feature weighting module 164 and determine domain scores for each of the domains. For each region, the domain scoring module 168 may cross-multiply the feature weights with the corresponding pre-processed feature values. The domain score for the domain can then be calculated and/or determined as an aggregated sum of the cross-multiplied aggregated weights and feature values. The domain scoring module 168 provides the domain scores for each region to a domain weighting module 172.

The domain weighting module 172 may be configured to receive the domain scores from the domain weighting module 172, and the census region data, rural census data and life expectancy data from the geographic-dependent database 112. The domain weighting module 172 may take as input the domain scores for each region and apply them to a quantile g-computation model to determine weights for each domain. The domain weights may indicate relative amounts of variation contributed by the respective domains to the life expectancy data of the regions. The quantile g-computation model may estimate the parameters of a marginal structural model that characterize the change in the expected potential outcome given a joint intervention on all exposures, possibly conditional on confounders. The quantile g-computation model may use the life expectancy data 144 as a dependent variable, the domain scores as independent variables, and the rural status data 148 and the census region data 152 as covariates. The domain weighting module 172 may output a weight for each domain. The domain weighting module 172 may provide the domain weights to the database 176 for storing.

When determining a region score of a specific region, a region scoring module 180 may request, and consequently receive, feature weights and domain weights from the database 176 and data for specified region, including the preprocessed feature values of the specified region, from the processed features database 160. In some examples, the region scoring module 180 may request and receive the inputs in response to receiving a request for a region score for the specified region.

The region scoring module 180 may determine a region domain score for each domain based on the feature weights for the features associated with the domain and the corresponding feature values in the data for the specified region. In some examples the region scoring module 180 may determine a region feature score for each feature of the domain by cross-multiplying the feature value and the feature weight associated with the feature. The region domain score can then be calculated as the sum of the region feature scores.

The region scoring module 180 may determine a region score for the region based on the region domain scores and corresponding domain weights. For example, the region scoring module 180 may cross-multiply each region domain score with the corresponding domain weight, and aggregate the cross-multiplication results to determine the region score. The region score may be a sum of the cross-multiplication results. The region scoring module 180 may determine the region scores for all regions of the geographical area in a similar manner.

The region scoring module 180 may provide the region score(s) to a user device 184 for presentation of the region scores. The region scoring module 180 may cause the user device 184 to transform a user interface of the user device to present and/or reflect the region score. In some examples, the region score may be presented in association with other data corresponding to the region, such as a geographical map or a region name. In some examples, the region score may be presented via a graphical user interface.

In some examples, the region scoring module 180 may provide the region score(s) to a classification module 188 for further analysis. The classification module 188 may perform classification analysis based on the region score(s). For example, the classification module 188 may classify the regions of the geographical area based on the region scores falling within classification ranges such as very high, high, medium, and low, with the higher classification indicating a higher need for additional resource in the corresponding region. The region scores for all regions may be classified within ranges derived by normalizing the region scores into the multiple ranges based on the concentration of the region scores between the scores of 0 and 100. In an example, the region score may be classified as (i) low for a score in the range of 0 and 27, (ii) medium for a score in the range of 27 and 37, (iii) high for a score in the range of 37 and 48, and (iv) very high for a score in the range of 48 and 100. The classification module 188 may be configured to classify the region scores using more, less, and/or alternate ranges. In another example, the region scores for the regions may be classified based on quartiles of the region scores, with (i) the bottom 25th percentile scores classified as low, (ii) the region scores between 26th and 50th percentile classified as medium, (iii) the region scores between 51 st and 75th percentile classified as high, and (iv) the top 25th percentile scores classified as very high. In some examples, the classification module 188 may decompose a region score to determine a percentage contribution of each domain on the region score.

The classification module 188 may be configured to receive a request for information from a user device 184 via an application programming interface. In response to the request, the classification module 188 may, in some examples, provide the classification(s) to the user device 184 for presentation. In some examples, the classification module 188 may use the classification(s) to automatically find resources to provide to a region.

In some examples, upon receiving a request from user device 184 of a user, such a physician, pharmacist, health care volunteer organization worker, or hospital worker, the classification module 188 may analyze, for a person residing in the region, the corresponding classification and percentage contribution to determine the high impact domains affecting the population of the region and determine social health resources to recommend to the person. In other examples, the classification module 188 may determine the high-impact domains affecting the population of the region based on the classification and/or percentage contributions, and determine resources that may be added by organizations to the region to best affect a positive change in the region score, thereby, allowing government and public organizations to effectively recognize the social health impediments faced by a region and add resources in an effective manner to improve the social health of the region. In another example, the classification module 188 may, for each person in an organization's database, such as patients of a hospital or doctor, determine a region based on the person's residential address and associate a classification associated with the region to the person's file in the database.

In some examples, the classification module 188 may perform a comparison analysis between the regions based on their corresponding regions scores. The analysis may indicate potential resources that may be added to a higher-classified region. In another example, the classification module 188 may be configured to aggregate or average the region scores of the regions belonging to a subset of the geographical area. The region score for a region may then be compared to the aggregated score of the subset to determine potential resources that can be distributed to the population of the region to bring the region score closer to the aggregated score. In some examples, the classification module 188 may be configured to compare a region score of the region at a current time with a region score of the same region at a previous time to determine a trend in the resource availability in the region. Similar analysis may be done with percentage contributions.

In some examples, the classification module 188 may perform a comparison between patients/clients with similar characteristics, such as diagnoses or certain healthcare benefits utilizations, and their respective region scores to determine whether a correlation exists between the region scores or domain percentage contributions and the client/patient characteristics. In another example, the classification module 188 may identify at-risk regions based on the classifications of the region and analyze the at-risk/under-resourced regions in association with clients/patients residing in those regions. In some examples, the classification module 188 may send the region classifications to a geographic information system ("GIS") or application to store, retrieve, map, and/or analyze geographic or spatial data based on the classifications. For example, the GIS or application may be used to generate geographic and/or spatial maps aligning the classifications with a volume of an organization's clients/patients living in the regions of the mapped geographical area to provide a visualization of comparison of resources available in different regions of the geographical area served by the organization. The results of the analysis by the classification module 188 may be caused to be presented on a user interface of the user device 184 based on a requested output.

Pre-Processor

Figure 2:
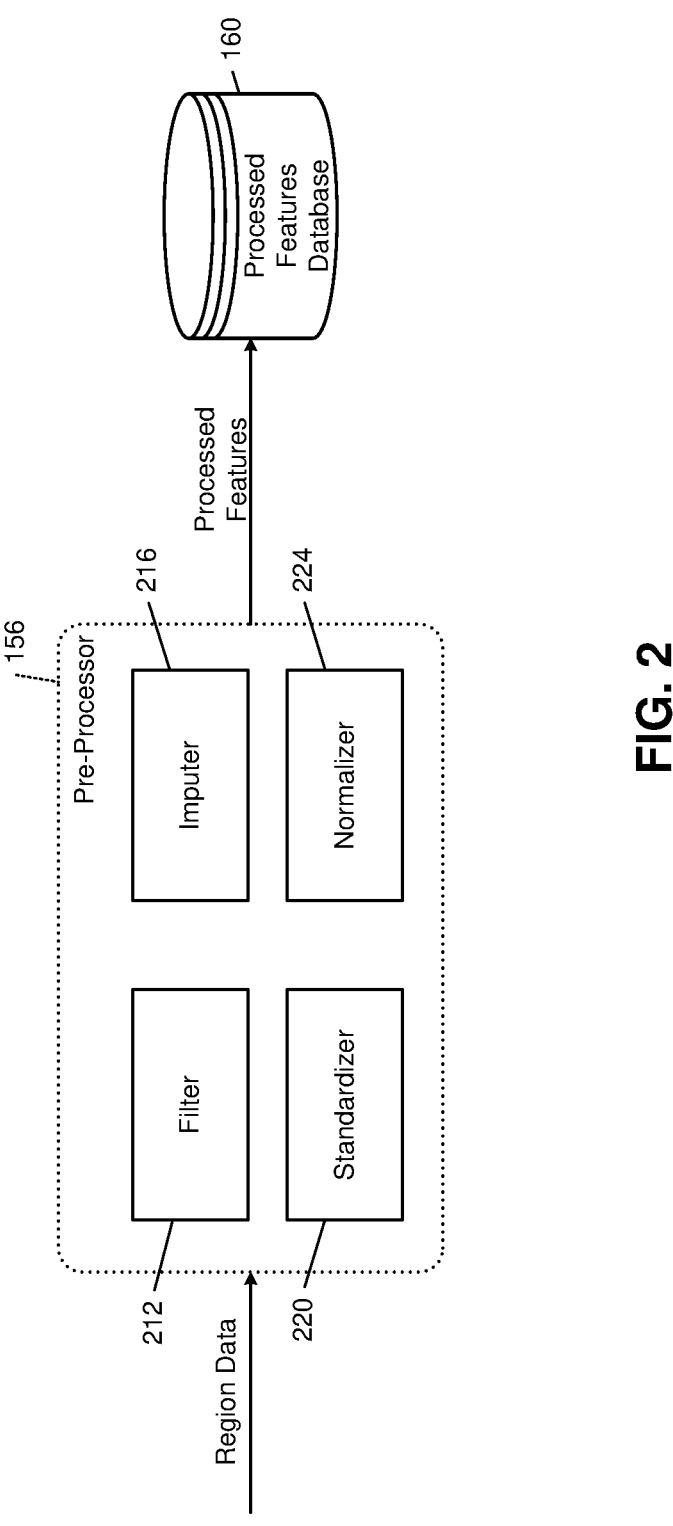
FIG. 2 is a block diagram of an example implementation of the preprocessor for determining social health according to aspects of the present disclosure.

FIG. 2 is an example implementation of the pre-processor 156. The pre-processor 156 receives as input region data from geographic-dependent database 112 and outputs pre-processed region data including processed features. The pre-processor 156 may include a filter 212, an imputer 216, a standardizer 220, and a normalizer 224.

The filter 212 may filter out data associated with one or more regions from the region data based on a filtering criteria. The filtering criteria may require removing data associated with regions with a majority of the population living in group homes that have controlled living environments, such as but not limited to, nursing homes, college dorms, military grounds, and prisons, as these communities may be outliers and are not affected by social factors in a similar way to other regions. In some examples, the filtering criteria may require removing data associated with regions with a population of less than five hundred people, less than a hundred households, and/or less than hundred housing units as inclusion of the population of these regions may be too small to reflect on other regions.

The imputer 216 may be configured to impute missing feature values in the region data with an average of the feature values of non-null neighbors (such as nearest 10) to complete the data set such that each feature in each domain of each region has a value associated with it. In some examples, feature values created using 2010 census geographies may be given tract assignment using a Census 2010 to 2020 Relationship file. A standardizer 220 may also be configured to trim feature values to fit within a predefined range. For example, the standardizer 220 may be configured to change a feature value that is lower than the range to a minimum value of the range, and a feature value that is higher than the range to a maximum value of the range. In some examples, the range may be from the first to the ninety-ninth percentile values of a feature; for such a feature, values lower than the first percentile can be changed to the first percentile value and values higher than the ninety-ninth percentile may be changed to the ninety-ninth percentile value.

Additionally or alternatively, the standardizer 220 may be configured to perform a log transformation on feature values to reduce skewness. For example, median household income as a ratio values, population-to-primary care physician as ratio values, population-to-pharmacy ratio values, median house value as ratio values, and/or pollutant concentration per capita values may be log transformed so that they fall between one and hundred. In some examples, the standardizer 220 may be configured to perform an inversion of values of a set of features such that lower values indicate a better access to resources for the population of the region than the higher values. For example, polarity of the values of features including the percentage of region area plus one mile occupied by impervious surface, percentage of households that responded to the census survey, median house value as a ratio, percentage of persons of ages between three and four enrolled in an educational institution, and/or median household income as a ratio may be switched so that a higher value corresponds to a worse access to resources.

In some examples, the standardizer 220 may additionally or alternatively be configured to perform a Z-score standardization on all values in the region data. For example, the standardizer 220 may standardize all values such that they center at mean zero and with a standard deviation of one for their respective features.

In some examples, the normalizer 224 may be configured to perform an inversion of values of features such that lower values indicate a better access to resources for the population of the region than higher values. For example, polarity of the values of features including the percentage of region area plus one mile occupied by impervious surface, percentage of households that responded to the census survey, median house value as a ratio, percentage of persons of ages three and four enrolled in an educational institution, and/or median household income as a ratio may be switched so that a higher value corresponds to a worse access to resources as compared to a lower value.

The pre-processed region data may be stored in the processed features database 160 as processed features. In some examples, the processed features database 160 may be located within the geographic-dependent database 112. In some examples, the processed features database 160 may be separate and/or located distinctly from the geographic-dependent database 112. In some other examples, the processed features database 160 may be the same as geographic-dependent database 112 with the features in the input region data replaced by the processed features in the pre-processed region data.

Feature Weighting Module and Domain Scoring Module

Figure 3:
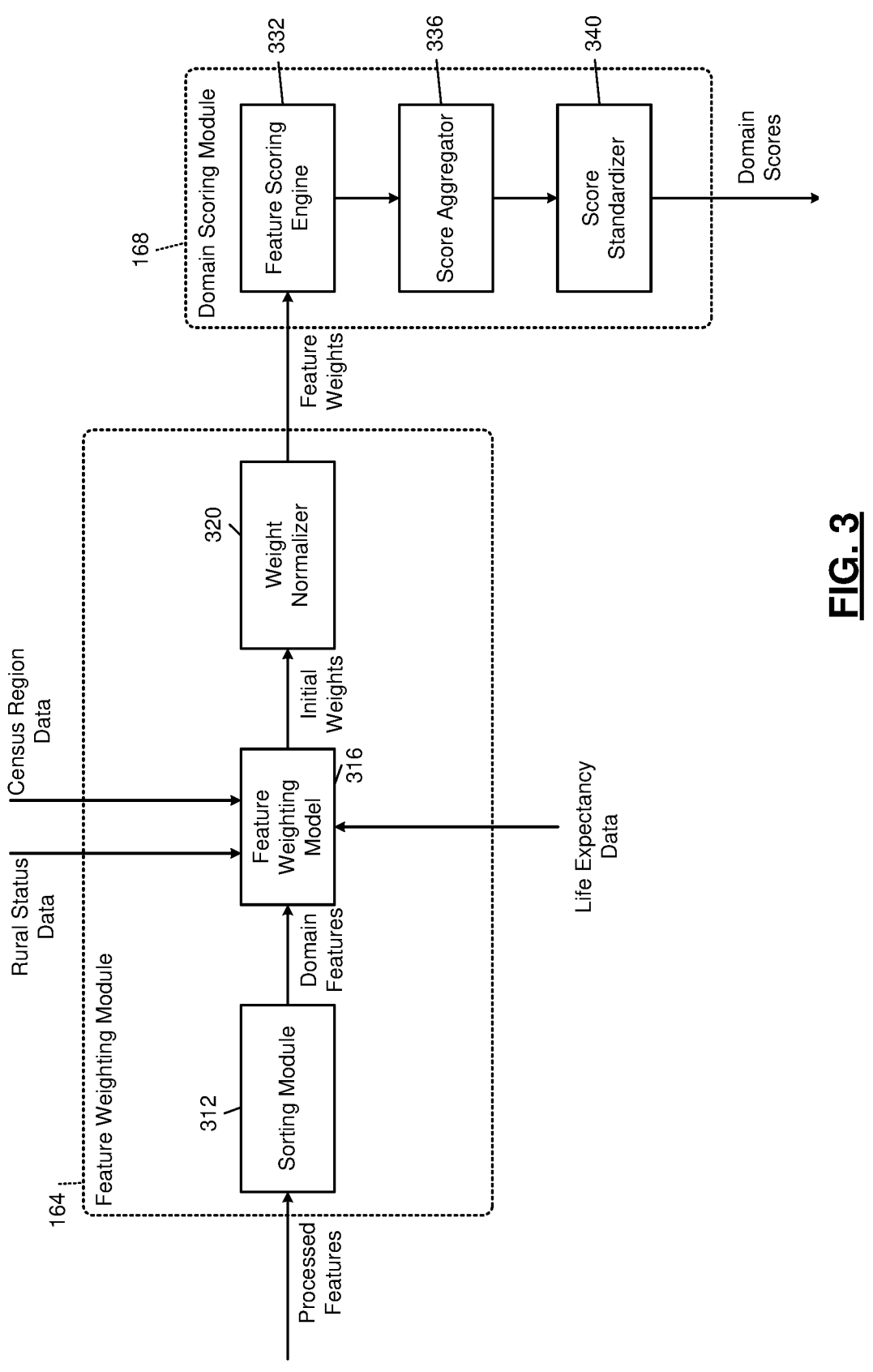
FIG. 3 is a block diagram of an example implementation of the feature weighting module and the domain scoring module according to aspects of the present disclosure.

FIG. 3 is an example implementation of the feature weighting module 164 and the domain scoring module 168 e. The feature weighting module 164 may receive and/or obtain the processed features from the pre-processor 156 and output feature weights for use by the domain scoring module 168 to determine domain scores. The feature weighting module 164 may include a sorting module 312, a feature weighting model 316, and a weight normalizer 320.

The sorting module 312 may sort the processed features into domain features for each domain. Domain features for a domain may include feature values for features of that domain, where each feature value is associated with a region of the geographical area. The feature weighting model 316 may receive as input the domain features sorted in accordance with individual domains and output initial weights for the features of the corresponding domains.

The feature weighting model 316 may be configured to estimate weights for the features of a domain. The feature weighting model 316 may determine the initial weights for the features of a domain based on the life expectancy values, the corresponding feature values, the rural status values, and the census region values for all regions. In some examples, the feature weighting model 316 may use the life expectancy values as a dependent variable, the feature values as independent variables, and the rural status and the census region values as covariates. The covariates may adjust the precision of the feature weighting model 316 to account for the effect of the urban regions and the composition of the census region on the model such that the distribution of the weights is increased for urban regions in the South census regions where the median income and cost of living is lower even for urban regions than those in the other census regions. The feature weighting model 316 may determine initial weights by estimating effect of increasing all features by one quantile simultaneously on the life expectancy values. It uses a "mixture effect" such that each feature is associated with a different weight to account for the multiple features being correlated. In some examples, the initial weights may be within a range of 0 and 1.

In some examples, the feature weighting model 316 may include a quantile g-function model. The quantile g-function model may estimate the parameters of a marginal structural model that characterizes the change in the expected life expectancy values given a join intervention on all exposures conditioned on the rural status values and the census region values. The quantile g-computation model does not require features to be directionally homogeneous. The quantile g-function model may allow for features to have different effects on the life expectancy values, thereby outputting different weights for each feature of a domain.

The feature weighting model 316 may use the following formula to determine the initial weights for features of a domain:

$$E\left(Y^{X_q} \mid Z, \psi, \eta\right) = g(\psi_0 + \psi_1 S_q + \eta Z);$$

where $g(\cdot)$ is a link function in a generalized linear model (the inverse logit function in the case of a logistic model for the probability that Y=1), $\psi$ is the model intercept, $\eta$ is a set of model coefficients for the covariates, and $S_q$ is an "index" that represents a joint value of exposures. Quantile g-computation may transform all exposures X into Xq, which are "scores" taking on discrete values 0, 1, 2, etc. representing a categorical "bin" of exposure. There may be ten bins with evenly spaced quantile cut points for each exposure, so Xq=0 means that X was below the observed 10th percentile for that exposure. The index $S_q$ represents all exposures being set to the same value (discrete values 0, 1, 2, 3, 5, 6, 7, 8, 9). The parameter/quantifies the expected change in the outcome, given a one quantile increase in all exposures simultaneously, possibly adjusted for Z. There may be fewer or more bins, and the percentiles for the exposures may be adjusted accordingly.

The quantile g-computation model may output coefficients for the features. The coefficients may be positive or negative indicating a relationship between the life expectancy values and the feature. The initial weight for a feature may be determined by dividing the absolute value of the coefficient by the sum of absolute values of all coefficients. In some examples, the quantile g-computation model may output multiple coefficients for each feature. In such examples, the initial weight for the feature may be determined by summing the absolute values of the feature coefficients and dividing it by the sum of the absolute values of all coefficients of all features. The initial weights may be in the range of 0 and 1.

The weight normalizer 320 may normalize the initial weights of the features to generate the feature weights for the features of the domain such that each feature weight is equal to or higher than 0.05. In some examples, a feature weight for a feature of a domain may be determined using the following formula:

$$FW = 0.05 + (IW * (1 - (0.05 * |F|)));$$

where FW is the feature weight, IW is the initial weight, and |F| is the total number of features in the domain. The normalizing technique described above is for example purposes only and other manners of normalizing the feature weights such that each feature weight is at least 0.05 are contemplated.

The feature weighting module 164 may determine feature weights for features of the other domains in a similar manner as described above and provide all feature weights for corresponding domains to the domain scoring module 168.

The domain scoring module 168 may determine domain scores for each domain for each region based on the corresponding feature weights. The domain scoring module 168 may include a feature scoring engine 332, a score aggregator 336, and a score standardizer 340. The feature scoring engine 332 may, for each region, receive the feature weights and apply them to the corresponding processed features for each domain to determine feature scores. The feature scores may be determined by cross-multiplying the feature weights and the corresponding processed feature values.

The score aggregator 336 may, for each region, determine an initial domain score for each domain by aggregating or summing the feature scores of the features corresponding to the domain. The score standardizer 340 may standardize the initial domain score to determine the domain score for a domain of a region. In some examples, the score standardizer 340 may standardize—for example using a z-score standardization technique—the initial domain scores to center at mean of zero and standard deviation of one for domain scores of the same domain for all regions. In some examples, the score standardizer 340 may normalize the initial scores to a range of zero to one such that initial domain scores lower than zero are changed to zero and the initial domain scores higher than one are changed to one. The score standardizer 340 may calculate the domain scores by multiplying the normalized scores by hundred such that the domain scores are within the range of zero to hundred. The domain scoring module 168 may determine domain scores for each domain for each region in this manner, and provide the domain scores to the domain weighting module 172 for determination of domain weights.

Domain Weighting Module and Domain Scoring Module

Figure 4:
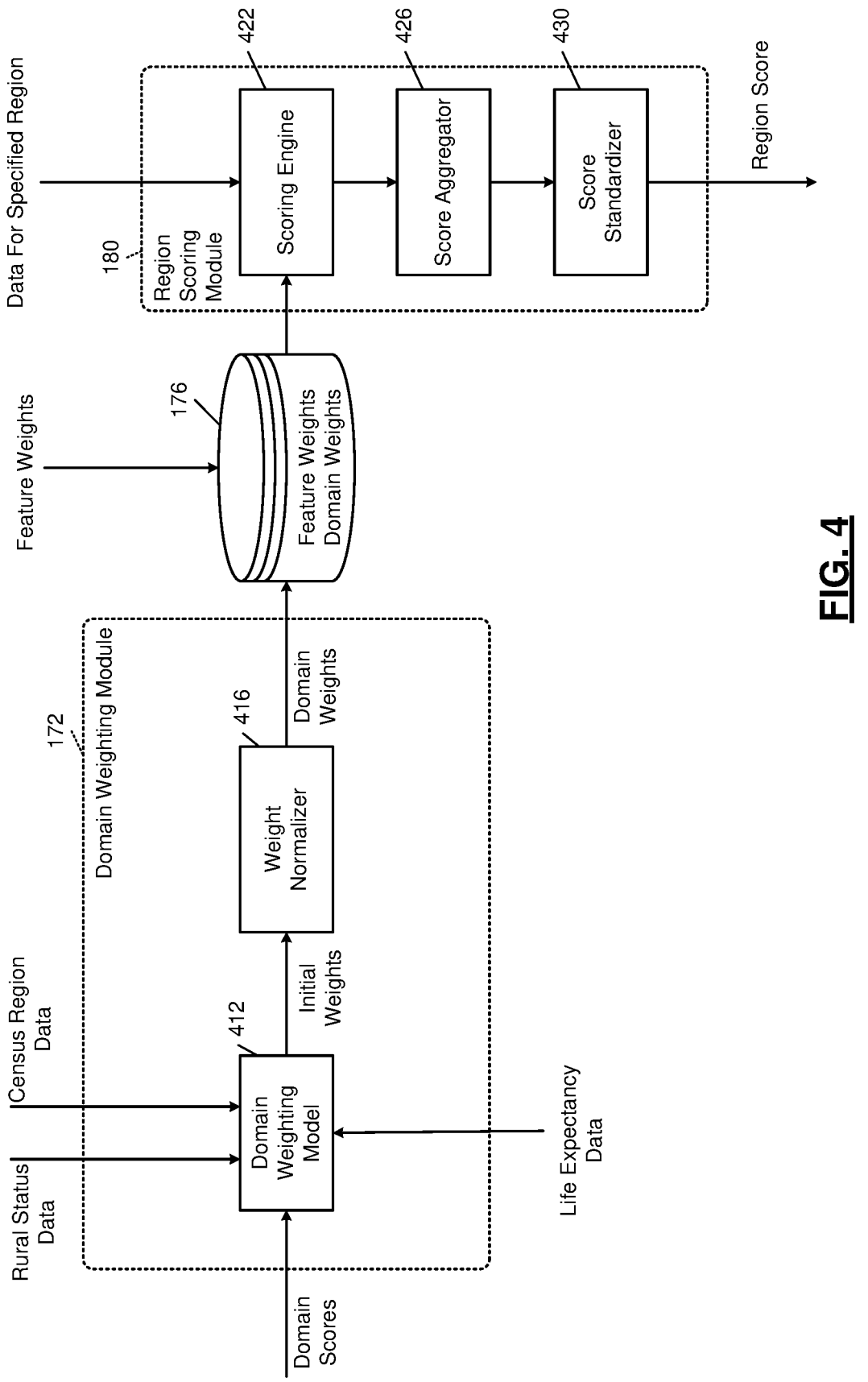
FIG. 4 is a block diagram of an example implementation of the domain weighting module and the region scoring module according to aspects of the present disclosure.

FIG. 4 is an example implementation of the domain weighting module 172 and the region scoring module 180. The domain weighting module 172 may receive and/or obtain the domain scores from the domain scoring module 168 and output domain weights for use by region scoring module 180 to determine region scores. The domain weighting module 172 may include a domain weighting model 412 and a weight normalizer 416.

The domain weighting model 412 may receive as input, for each region, the domain scores for the corresponding domains and output initial weights for the domains. The domain weighting model 412 may be configured to estimate weights for each domain. The domain weighting model 412 may determine the initial weights for the domains based on the life expectancy values, the corresponding domain scores, the rural status values and the census region values for all regions. In some examples, the domain weighting model 412 may use the life expectancy values as a dependent variable, the domain scores as the independent variables, and the rural status and the census region values as covariates. The covariates may adjust the precision of the domain weighting model 412 to account for the effect of the urban regions and the composition of the census region on the model such that the distribution of the weights is increased for urban regions in the South census regions where the median income and cost of living is lower even for urban regions than those in the other census regions. The domain weighting model 412 may determine initial weights by estimating effects of increasing all domain scores by one quantile simultaneously on the life expectancy values. It uses a "mixture effect" such that each domain is associated with a different weight to account for the multiple domains being correlated. In some examples, the initial weights may be within a range of 0 and 1.

In some examples, the domain weighting model 412 may include a quantile g-function model. The quantile g-function model may estimate the parameters of a marginal structural model that characterizes the change in the expected life expectancy values given a join intervention on all exposure conditioned on the rural status values and the census region values. The quantile g-computation model does not require the domains to be directionally homogeneous. The quantile g-function model may allow for domains to have different effects on the life expectancy values, thereby outputting different weights for each domain.

The domain weighting model 412 may use the following formula to determine the initial weights for the domains:

$$E(Y^{X_q} \mid Z, \psi, \eta) = g(\psi_0 + \psi_1 S_q + \eta Z);$$

where $g(\cdot)$ is a link function in a generalized linear model (the inverse logit function in the case of a logistic model for the probability that Y=1), $\psi$ is the model intercept, $\eta$ is a set of model coefficients for the covariates, and $S_q$ is an "index" that represents a joint value of exposures. Quantile g-computation may transform all exposures X into Xq, which are "scores" taking on discrete values 0, 1, 2, etc. representing a categorical "bin" of exposure. There may be ten bins with evenly spaced quantile cut points for each exposure, so Xq=0 means that X was below the observed 10th percentile for that exposure. The index $S_q$ represents all exposures being set to the same value (discrete values 0, 1, 2, 3, 4, 5, 6, 7, 8, 9). The parameter $\psi$ quantifies the expected change in the outcome, given a one quantile increase in all exposures simultaneously, possibly adjusted for Z. It should be noted that there may be fewer or more bins and the percentiles for the exposures may be adjusted accordingly.

The quantile g-computation model may output coefficients for the domains. The coefficients may be positive or negative indicating a relationship between the life expectancy values and the domain. The initial weight for a domain may be determined by dividing the absolute value of the coefficient by the sum of absolute values of all coefficients for all domains. In some examples, the quantile g-computation model may output multiple coefficients for each domain. In such examples, the initial weight for the domain may be determined by summing the absolute values of the domain coefficients and dividing it by the sum of absolute values of all coefficients of all domains. The initial weights may be in the range of 0 and 1.

The weight normalizer 416 may normalize the initial weights of the domains to generate the domain weights such that each domain weight is equal to or higher than 0.05. In some examples, a domain weight for a domain may be determined using the following formula:

$$DW = 0.05 + (IW * (1 - (0.05 * |D|)))$$

where FW is the domain weight, IW is the initial weight, and |D| is the total number of domains. The normalizing technique described above is for example purposes only and other manners of normalizing the domain weights such that each domain weight is at least 0.05 are contemplated.

The region scoring module 180 may determine a region score for each region based on the processed feature values for the region, the feature weights, and the domain weights. The region scoring module 180 may include a scoring engine 422, a score aggregator 426, and a score standardizer 430. The scoring engine 422 may, receive the feature weights and apply them to the corresponding processed features for each domain to determine individual feature scores. The individual feature scores may be determined by cross-multiplying the feature weights and the corresponding processed feature values. The scoring engine 422 may determine region domain scores by cross-multiplying the domain weights and the sum of the individual feature scores of the corresponding domains.

The score aggregator 426 may determine an initial region score for the region by aggregating or summing the initial domain scores of the domain. The domain scoring module 168 may determine region scores for each region of the geographical area in this manner.

The score standardizer 430 may standardize the initial region scores to determine the final region scores for the regions. In some examples, the score standardizer 430 may standardize the initial region scores to center at mean of zero and standard deviation of one. In some examples, the score standardizer 430 may normalize the initial region scores to a range of zero to one such that initial region scores lower than zero are changed to zero and the initial region scores higher than one are changed to one. The score standardizer 430 may calculate the region score for a region by multiplying the normalized score by hundred such that the region score is within the range of zero to hundred. The domain scoring module 168 may provide the region scores to the classification module 188 for further analysis and/or the user device 184 for transforming a user interface, such as a graphical user interface of the user device, to reflect the region score(s).

Process Flowcharts

Figure 5A:
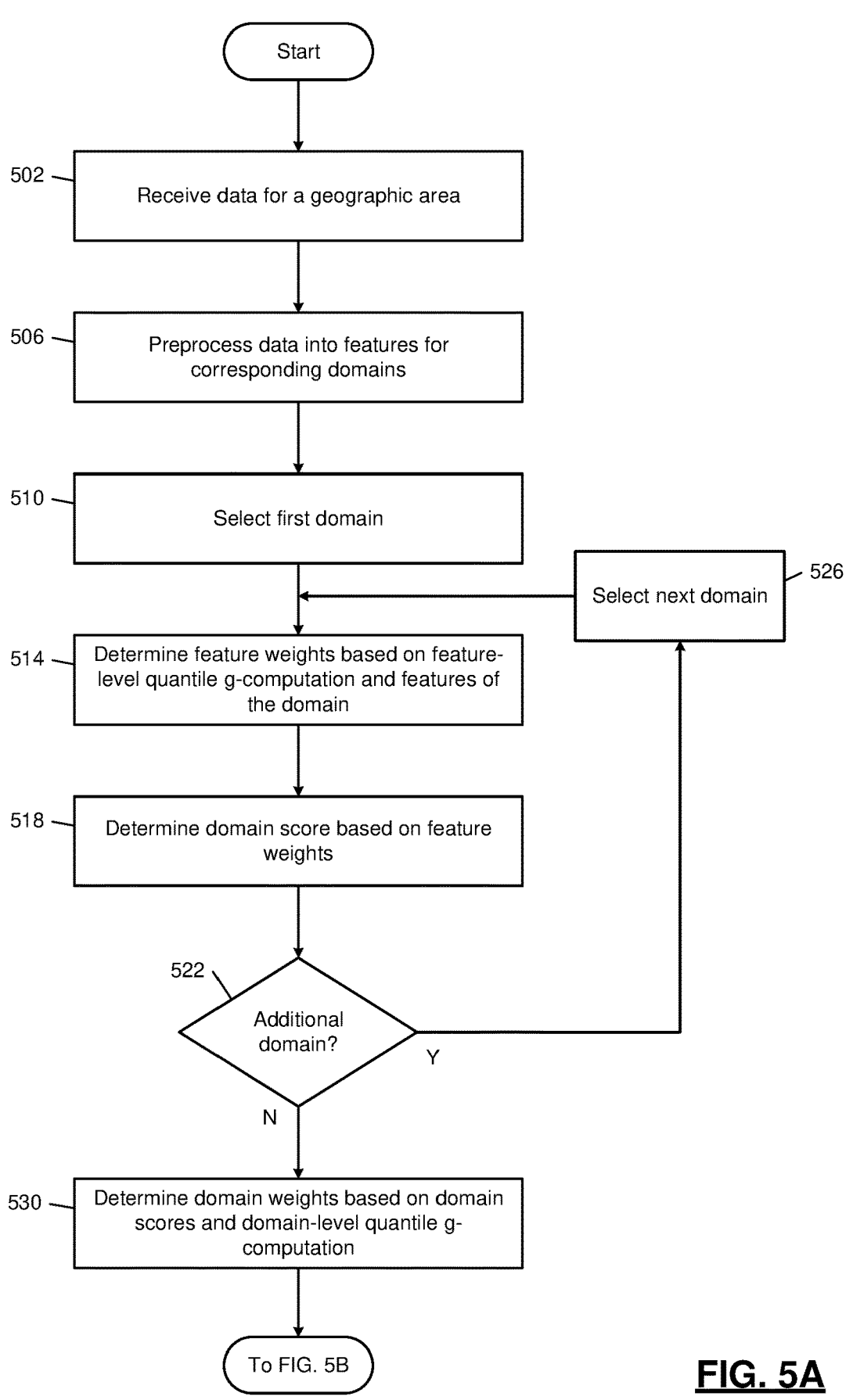
FIGS. 5A-5B together are a flowchart of a first computer-implemented method for determining social health of a region according to aspects of the present disclosure.

In FIG. 5A, processing—for example, by a social health determination system—begins at 502. At 502, control receives data for a geographic area. For example, the pre-processor 156 may receive region data from the geographic-dependent database 112. Control transfers to 506. At 506, control preprocesses the geographic data into features for corresponding domains. For example, the pre-processor 156 may process the region data into processed features for each region, with each feature corresponding to a domain. Control transfers to 510.

At 510, control selects a first domain. For example, the feature weighting module 164 may select a domain for which to determine feature weights. Control transfers to 514. At 514, control determines feature weights based on feature-level quantile g-computation and features of the domain. Control transfers to 518.

At 518, control determines a domain score based on feature weights. For example, the domain scoring module 168 may determine a domain score for the domain by cross-multiplying the feature weights and the corresponding feature values. Control transfers to 522.

At 522, control determines whether there is an additional domain. If so, control transfers to 526, and otherwise control transfers to 530. At 526, control selects a next domain. For example, the feature weighting module 164 may select a next domain for analysis after calculating the feature weights for features of a previous domain until all domains have been analyzed. Control transfers back to 514.

Figure 5B:
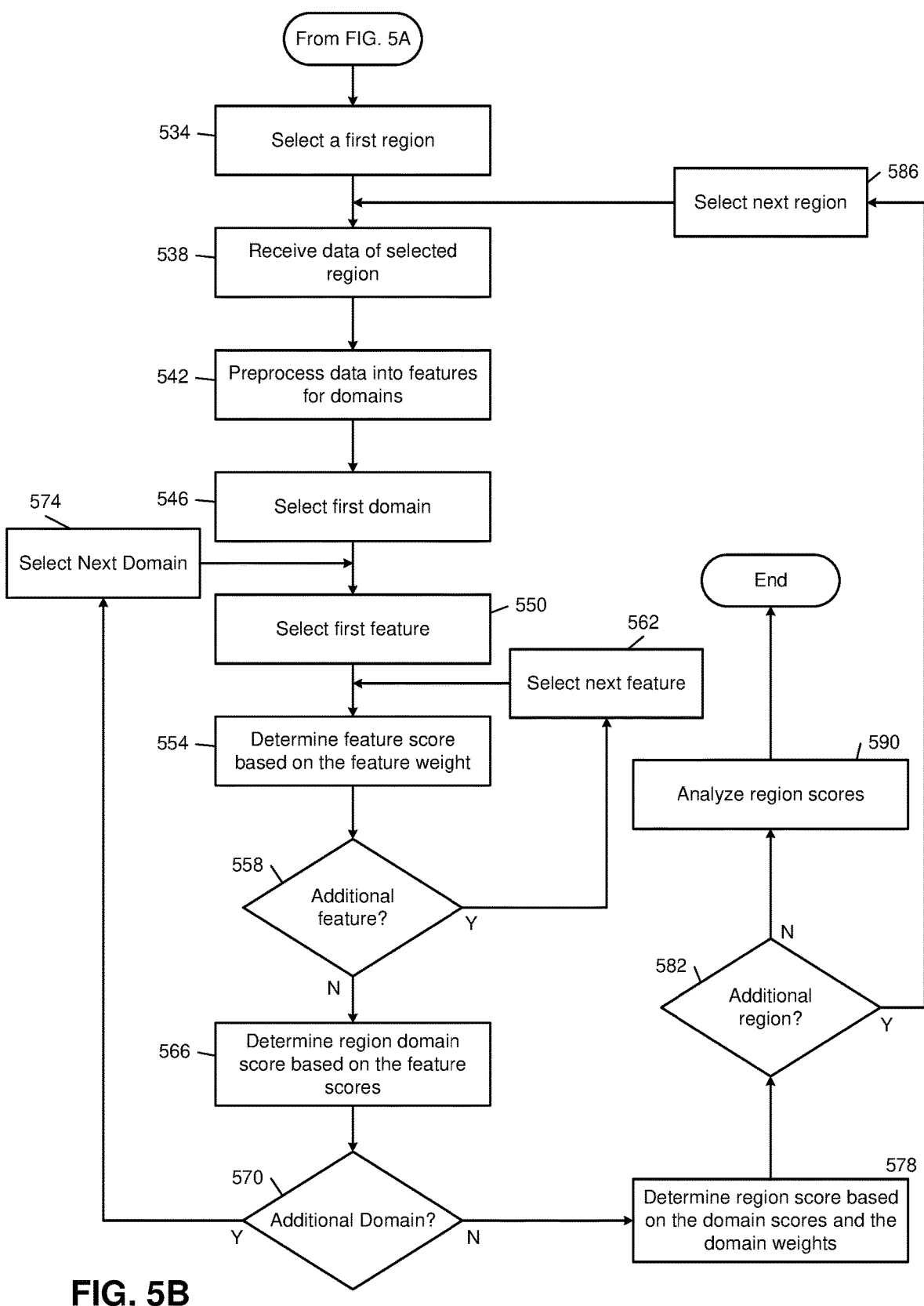

At 530, control determines domain weights based on domain scores and domain-level quantile g-computation. For example, once domain scores for all domains have been determined, the domain weighting module 172 may determine domain weights based on the domain scores and another quantile g-computation model. Control transfers to 534 of FIG. 5B.

At 534, control selects a first region. For example, the region scoring module may select a region of the geographical area for calculating final region score for the region. Control transfers to 538. At 538, control receives data of selected region. For example, the region scoring module 180 may receive processed features for the selected region from the processed features database 160. Control transfers to 542.

At 542, control preprocessed data into features for domains. For example, pre-processor 156 may sort the data for specified region into domains, each domain including feature values for features corresponding to the domain. Control transfers to 546. At 546, control selects a first domain. For example, the region scoring module 180 may select a first domain for determining a region domain score for the region. Control transfers to 550. At 550, control selects a first feature. For example, the region scoring module 180 may select a first feature of the domain to determine a feature score. Control transfers to 554.

At 554, control determines a feature score based on the feature weight. For example, the scoring engine 422 may determine a feature score for the selected feature of the domain based on cross-multiplying the feature weight of the feature and a feature value of the feature in the processed features of the region. Control transfers to 558.

At 558, control determines whether there is an additional feature. If so, control transfers to 562; otherwise, control transfers to 566. At 562, control selects the next feature. For example, the region scoring module 180 may select another feature of the selected domain to determine a feature score until all features of the domain have been scored. Control transfers back to 554.

At 566, control determines a region domain score based on the feature scores. For example, the scoring engine 422 may determine a region domain score for the domain as an aggregate or sum of the feature scores of the features of the domain. Control transfers to 570.

At 570, control determines whether there is an additional domain for the region. For example, the region scoring module 180 may determine whether there are additional domains remaining for the region. If so, control transfers to 574, otherwise control transfers to 578. At 574, control selects next domain. For example, the region scoring module 180 may select the next domain for determining a region domain score until all domains have been scored. Control transfers back to 550.

At 578, control determines a region score based on the domain scores and the domain weights. For example, the region scoring module 180 may determine a region score by cross-multiplying the domain scores and the corresponding domain weights. Control transfers to 582.

At 582, control determines whether there is an additional region to score. If so, control transfers to 586, otherwise control transfers to 590. At 586, control selects the next region. For example, the region scoring module 180 may continue to calculate region scores for regions until it has determined a region score for all regions of the geographical area. Control transfers back to 538.

At 590, control analyzes the regional scores. For example, the classification module 188 may classify the regions based on the regional scores and perform an action, such as a comparison analysis, based on the region scores/classifications. Control ends at 590.

In FIG. 6, processing—for example, by a social health determination system—begins at 602. At 602, control receives first data for a geographical area, where the first data includes values for multiple features, and where the features correspond to multiple domains. For example, the feature weighting module 164 receives processed features for a geographical region including feature values of features corresponding to domains from processed features database 160. Control transfers to 606.

At 606, for a first domain of the multiple domains, control selects a set of features that correspond to the first domain from the multiple features. For example, the feature weighting module 164 may select a set of features from the multiple features that corresponds to a first domain of multiple domains. Control transfers to 610.

At 610, control determines feature weights for the set of features based on a feature-level quantile g-computation of the values of the first data for the set of features, wherein the feature weights indicate relative amounts of variation contributed by the respective features to the first domain. For example, the feature weighting module 164 may determine feature weights for the features of the first domain based on the values of the features and the feature weighting model 316. The feature weights indicate relative amounts of variation contributed by the respective features to the domain. Control transfers to 614.

At 614, control receives second data for a region of the geographical area, wherein the second data includes values for a subset of the multiple features. For example, the region scoring module 180 may receive feature values corresponding to at least some of the features for a region of the geographical area from the processed features database 160. Control transfers to 618.

At 618, for the first domain, control determines a region domain score based on the second data and the feature weights. For example, the region scoring module 180 may determine a domain score for the domain based on cross-multiplying the feature weights with their corresponding feature values in the second data and summing the cross-multiplied values. Control transfers to 622.

At 622, control determines a total score for the region based on the region domain score, wherein the total score indicates a level of resource access for a population of the region. For example, the region scoring module 180 may determine the region score for the region based on aggregating the domain scores of all domains. Control transfers to 626.

At 626, control transforms a user interface to reflect the total score. For example, the region score may be presented to a user on a user device via a user interface, such as a graphical user interface. Control then ends.

The domain scoring can be used in conjunction with the Shipping Disruption Predictive Technology as described in U.S. patent application Ser. No. 17/514,444, filed 5 May 2022, which is hereby incorporated by reference. The domain scoring or the total score for a region can incorporate data types from the Shipping Disruption Predictive Technology patent application, e.g., current events, current conditions in a domain or region or likelihood of future events or future conditions that may affect the delivery of medications in the given geographic area.

Conclusion

The foregoing description is merely illustrative in nature and is in no way intended to limit the disclosure, its application, or uses. The broad teachings of the disclosure can be implemented in a variety of forms. Therefore, while this disclosure includes examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in a different order (or concurrently) without altering the principles of the present disclosure. Unless indicated otherwise, numbering, or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements as well as an indirect relationship where one or more intervening elements are present (either spatially or functionally) between the first and second elements.

As noted below, the term "set" generally means a grouping of one or more elements. However, in various implementations a "set" may, in certain circumstances, be the empty set (in other words, the set has zero elements in those circumstances). As an example, a set of search results resulting from a query may, depending on the query, be the empty set. In contexts where it is not otherwise clear, the term "non-empty set" can be used to explicitly denote exclusion of the empty set—that is, a non-empty set will always have one or more elements.

A "subset" of a first set generally includes some of the elements of the first set. In various implementations, a subset of the first set is not necessarily a proper subset: in certain circumstances, the subset may be coextensive with (equal to) the first set (in other words, the subset may include the same elements as the first set). In contexts where it is not otherwise clear, the term "proper subset" can be used to explicitly denote that a subset of the first set must exclude at least one of the elements of the first set. Further, in various implementations, the term "subset" does not necessarily exclude the empty set. As an example, consider a set of candidates that was selected based on first criteria and a subset of the set of candidates that was selected based on second criteria; if no elements of the set of candidates met the second criteria, the subset may be the empty set. In contexts where it is not otherwise clear, the term "non-empty subset" can be used to explicitly denote exclusion of the empty set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" can be replaced with the term "controller" or the term "circuit" or the term "circuitry." In this application, the term "controller" can be replaced with the term "module."

The term "module" may refer to, be part of, or include processor hardware or processing circuitry (shared, dedicated, or group) that executes code coupled with memory hardware (shared, dedicated, or group) that stores code executed by the processor hardware.

The module may include one or more interface circuit(s). In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2020 (also known as the WIFI wireless networking standard) and IEEE Standard 802.3-2018 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

The memory hardware may also store data together with or separate from the code. Shared memory hardware encompasses a single memory device that stores some or all code from multiple modules. One example of shared memory hardware may be level 1 cache on or near a microprocessor die, which may store code from multiple modules. Another example of shared memory hardware may be persistent storage, such as a solid state drive (SSD) or magnetic hard disk drive (HDD), which may store code from multiple modules. Group memory hardware encompasses a memory device that, in combination with other memory devices, stores some or all code from one or more modules. One example of group memory hardware is a storage area network (SAN), which may store code of a particular module across multiple physical devices. Another example of group memory hardware is random access memory of each of a set of servers that, in combination, store code of a particular module. The term memory hardware is a subset of the term computer-readable medium.

The apparatuses and methods described in this application may be partially or fully implemented by a special purpose computer created by configuring computer circuitry to execute one or more particular functions embodied in computer programs. Such apparatuses and methods may be described as computerized or computer-implemented apparatuses and methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The term non-transitory computer-readable medium does not encompass transitory electrical or electromagnetic signals propagating through a medium (such as on a carrier wave). Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The term "set" generally means a grouping of one or more elements. The elements of a set do not necessarily need to have any characteristics in common or otherwise belong together. The phrase "at least one of A, B, and C" should be construed to mean a logical (A OR B OR C), using a non-exclusive logical OR, and should not be construed to mean "at least one of A, at least one of B, and at least one of C." The phrase "at least one of A, B, or C" should be construed to mean a logical (A OR B OR C), using a non-exclusive logical OR.

The invention claimed is:

1. A computer-implemented method for determining a social health score for a region, the computer-implemented method comprising:

receiving, at processor hardware, first data for a geographical area, wherein the first data includes values for a plurality of features, and wherein the plurality of features corresponds to a plurality of domains;

for a first domain of the plurality of domains:

from the plurality of features, selecting a first set of features that correspond to the first domain, and determining, via the processor hardware, first feature weights for the first set of features based on a feature-level quantile g-computation of the values of the first data for the first set of features, wherein the first feature weights indicate relative amounts of variation contributed by the respective features to the first domain;

receiving, at the processor hardware, second data for the region of the geographical area, wherein the second data includes values for a subset of the plurality of features;

determining, via the processor hardware, whether the first domain is a first domain type;

in response to a determination that the first domain is the first domain type, determining, via the processor hardware, a mean value for a respective feature of the subset of the plurality of features by:

identifying an area of an image in the second data corresponding to the region, determining a pixel value average of the area of the image, and assigning the pixel value average as the mean value;

for the first domain, determining, via the processor hardware, a first region domain score based on the second data and the first feature weights;

determining, via the processor hardware, a total score for the region based on the first region domain score, wherein the total score indicates a level of resource access for a population of the region; and transforming a user interface to reflect the total score.

2. The computer-implemented method of claim 1 wherein the total score indicates a level of impediment for the population of the region of the geographical area to access resources.

3. The computer-implemented method of claim 1 further comprising:

determining feature scores for the subset of the plurality of features by cross-multiplying the first feature weights and the values of the second data, and determining the first region domain score based on the feature scores.

4. The computer-implemented method of claim 3 wherein determining the first region domain score includes aggregating the feature scores.

5. The computer-implemented method of claim 1 further comprising:

for a second domain of the plurality of domains:

from the plurality of features, selecting a second set of features that correspond to the second domain, and determining second feature weights for the second set of features based on the feature-level quantile g-computation of the values of the first data for the second set of features, wherein the second feature weights indicate relative amounts of variation contributed by the respective features to the second domain; and for the second domain, determining a second region domain score based on the second data and the second feature weights, wherein the total score of the region is based on aggregating the first region domain score and the second region domain score.

6. The computer-implemented method of claim 1 wherein there is a one-to-one correspondence between the first feature weights and the first set of features.

7. The computer-implemented method of claim 1 further comprising in response to the subset being a proper subset, fill in those missing features of the second data.

8. The computer-implemented method of claim 1 wherein the region is a United States census tract.

9. The computer-implemented method of claim 1 further comprising:

determining a domain score for the first domain based on the first feature weights and the first data;

determining a domain weight for the first domain based on a domain-level quantile g-computation applied to the domain score, wherein the domain weight indicates a relative variation the first domain contributes to the geographical area; and determining the first region domain score based on the domain weight.

10. The computer-implemented method of claim 9 further comprising:

determining feature scores based on cross-multiplying the first feature weights and the values of the second data; and determining the first region domain score based on cross-multiplying the domain weight and the feature scores.

11. The computer-implemented method of claim 1 wherein the plurality of domains includes seven domains, and the plurality of features includes twenty-eight features.

12. The computer-implemented method of claim 1 further comprising preprocessing the values for the plurality of features to fit within a range.

13. The computer-implemented method of claim 12 wherein fitting the values within the range includes changing at least one value that is lower than the range to a minimum value of the range.

14. The computer-implemented method of claim 12 wherein fitting the values within the range includes changing at least one value that is higher than the range to a maximum value of the range.

15. The computer-implemented method of claim 1 wherein none of the first feature weights are below five percent.

16. The computer-implemented method of claim 1 wherein:

the first data includes:

a plurality of life expectancy values for a plurality of regions of the geographical area, a plurality of rural status values for the plurality of regions, and a plurality of census region values for the plurality of regions; and the first feature weights are determined based on the plurality of life expectancy values, the plurality of rural status values, and the plurality of census region values.

17. A system for determining a scoring a region, the system comprising:

a database including:

first data for a geographical area, wherein the first data includes values for a plurality of features, and wherein the plurality of features corresponds to a plurality of domains, and second data for the region of the geographical area, wherein the second data includes values for a subset of the plurality of features;

a weighting module configured to, for a first domain of the plurality of domains:

from the plurality of features, select a first set of features that correspond to the first domain, and determine, via processor hardware, first feature weights for the first set of features based on a feature-level quantile g-computation of the values of the first data for the first set of features, wherein the first feature weights indicate relative amounts of variation contributed by the respective features to the first domain;

a domain scoring module configured to;

determine, via the processor hardware, whether the first domain is a first domain type;

in response to a determination that the first domain is the first domain type, determine, via the processor hardware, a mean value for a respective feature of the subset of the plurality of features by:

identifying an area of an image in the second data corresponding to the region, determining a pixel value average of the area of the image, and assigning the pixel value average as the mean value; and determine, via the processor hardware, for the first domain, a first region domain score based on the second data and the first feature weights;

a region scoring module configured to determine, via the processor hardware, a total score for the region based on the first region domain score, wherein the total score indicates a level of resource access for a population of the region; and a user interface to reflect the total score.

18. The system of claim 17 wherein the domain scoring module is configured to:

determine feature scores for the subset of the plurality of features by cross-multiplying the first feature weights and the values of the second data, and determining the first region domain score based on the feature scores.

19. The system of claim 17 wherein:

the weighting module is configured to, for a second domain of the plurality of domains:

from the plurality of features, select a second set of features that correspond to the second domain, and determine second feature weights for the second set of features based on the feature-level quantile g-computation of the values of the first data for the second set of features, wherein the second feature weights indicate relative amounts of variation contributed by the respective features to the second domain;

the domain scoring module is configured to, for the second domain, determine a second region domain score based on the second data and the second feature weights; and the region scoring module is configured to determine the total score of the region based on aggregating the first region domain score and the second region domain score.

20. A non-transitory computer-readable medium comprising instructions including:

receiving, at processor hardware, first data for a geographical area, wherein the first data includes values for a plurality of features, and wherein the plurality of features corresponds to a plurality of domains;

for a first domain of the plurality of domains:

from the plurality of features, selecting a first set of features that correspond to the first domain, and determining, via the processor hardware, first feature weights for the first set of features based on a feature-level quantile g-computation of the values of the first data for the first set of features, wherein the first feature weights indicate relative amounts of variation contributed by the respective features to the first domain;

receiving, at the processor hardware, second data for a region of the geographical area, wherein the second data includes values for a subset of the plurality of features;

determining, via the processor hardware, whether the first domain is a first domain type;

in response to a determination that the first domain is the first domain type, determining, via the processor hardware, a mean value for a respective feature of the subset of the plurality of features by:

identifying an area of an image in the second data corresponding to the region, determining a pixel value average of the area of the image, and assigning the pixel value average as the mean value;

for the first domain, determining, via the processor hardware, a first region domain score based on the second data and the first feature weights;

determining, via the processor hardware, a total score for the region based on the first region domain score, wherein the total score indicates a level of resource access for a population of the region; and transforming a user interface to reflect the total score.

* * * * *